United States Patent [19]
Mesek

[11] 4,136,698
[45] Jan. 30, 1979

[54] DIAPER WITH TAB FASTENER HAVING GRIPPABLE ADHESIVE-FREE END REGION

[75] Inventor: Frederick K. Mesek, Downers Grove, Ill.

[73] Assignee: Johnson & Johnson, New Brunswick, N.J.

[21] Appl. No.: 734,204

[22] Filed: Oct. 20, 1976

[51] Int. Cl.² ............................................. A61F 13/16
[52] U.S. Cl. .................................... 128/287; 128/284
[58] Field of Search ............... 128/284, 287, 290 R, 128/67; 24/DIG. 11, 73 VA; 428/41

[56] References Cited

U.S. PATENT DOCUMENTS

| | | | |
|---|---|---|---|
| 3,776,234 | 12/1973 | Hoey | 128/287 |
| 3,794,038 | 2/1974 | Buell | 128/287 |
| 3,833,456 | 9/1974 | Reed | 128/287 X |
| 3,840,013 | 10/1974 | Mesek | 128/287 |
| 3,848,594 | 11/1974 | Buell | 128/284 |
| 3,848,594 | 11/1974 | Buell | 128/284 |
| 3,860,003 | 1/1975 | Buell | 128/287 |
| 3,987,793 | 10/1976 | Milmanow | 128/287 |
| 3,999,546 | 12/1976 | Feldman | 128/284 |

Primary Examiner—John D. Yasko

[57] ABSTRACT

A disposable diaper is provided with adhesive tabs having gripping means to facilitate separation of the tab from release means preparatory to fastening the diaper about an infant. The adhesive tabs comprise a backing web which extends around and receives a marginal portion of the diaper, and a face web having continuous coating of adhesive on one face and a grippable adhesive-free region at one end. The face web comprises a fixed end permanently attached to one leg of the backing web, and an adhesive-coated free working portion situated between the fixed end and the grippable adhesive-free region. When the tab fastener is in a storage position, the free working portion is releasably attached to release means provided on the other leg of the backing web and the adhesive-free region extends inwardly from a lateral margin of the diaper and beyond the release means, so that it can be gripped for separating the free working portion from the release means when securing the diaper about an infant.

10 Claims, 6 Drawing Figures

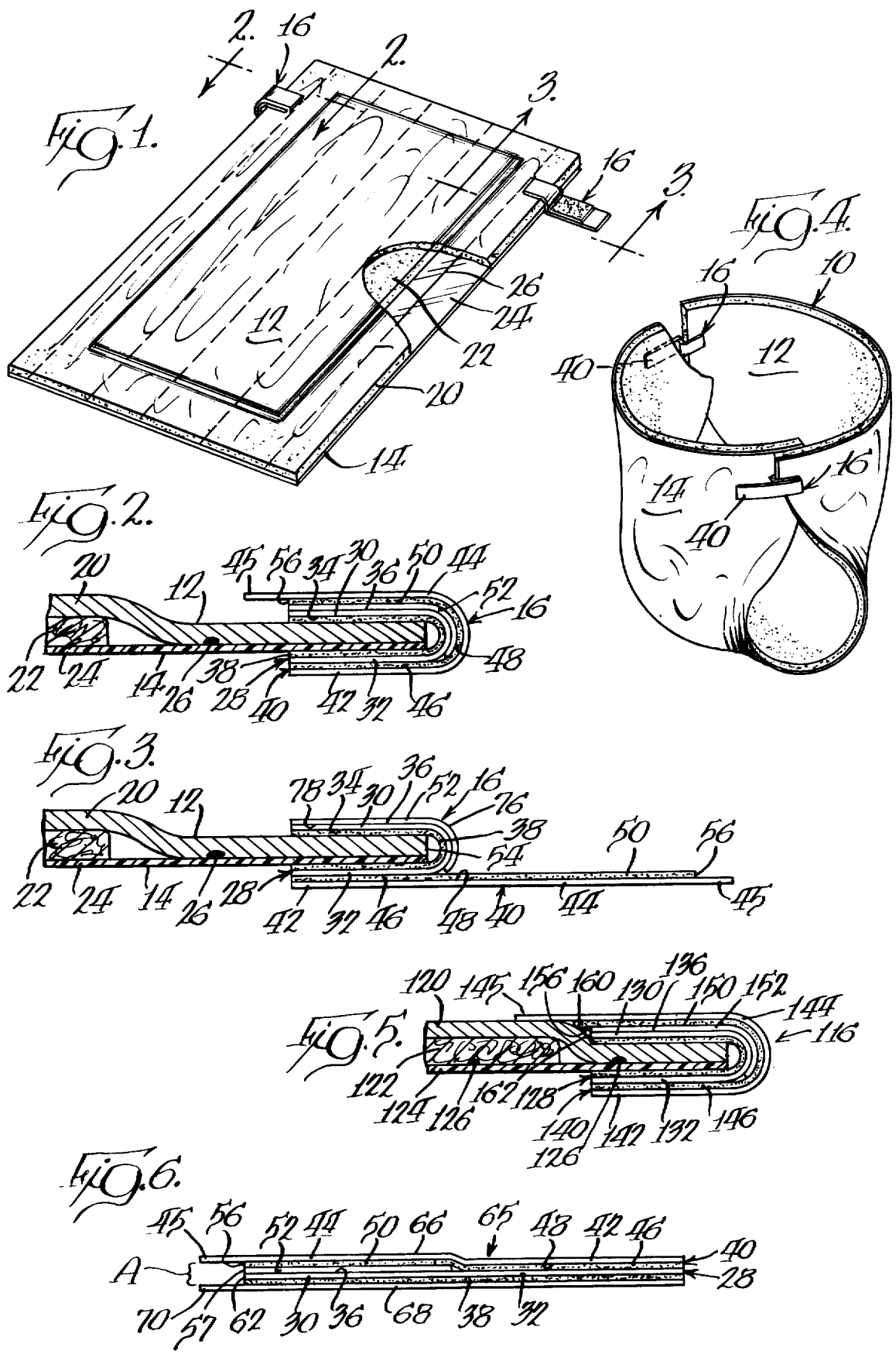

DIAPER WITH TAB FASTENER HAVING GRIPPABLE ADHESIVE-FREE END REGION

BACKGROUND OF THE INVENTION

This invention relates to disposable diapers. More particularly, this invention relates to disposable diapers adapted to be secured in place by adhesive tabs.

Disposable diapers provide substantial advantages in convenience over diapers intended to be laundered and reused, particularly when they are used away from home. In recent years, many different diposable diapers have been proposed and some have been successful in the marketplace. Typical disposable diaper structures comprise a moisture-retaining layer of high liquid-holding capacity and a moisture-impervious backing sheet therefor, generally made of a plastic film such as polyethylene film or the like. Typical disposable diaper structures are shown in U.S. Pat. No. 3,612,055 to Mesek et al. and in U.S. Pat. No. Re. 26,151 to Duncan et al.

As may be seen from the above-cited patents, it is desirable to obviate the problems that are inherent in closure systems which utilize extraneous fasteners such as safety pins, snaps and zippers. To this end adhesive closure systems have presented acceptable solutions.

In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper.

U.S. Pat. No. 3,616,114 to Hamaguchi et al. discloses an adhesive sealing tape which can be used for releasably interconnecting parts of a diaper or other container. The fixed end of a main tape portion is attached to one side of a first container part. A reinforcing tape portion is provided with a turned up end which is attached to the undersurface of the midregion of the main tape portion, and a part of the reinforcing tape portion is attached to the opposite side of the first container part. The free end of the main tape portion is adapted for attachment to a second container part which is to be secured to the first container part. Thus, the Hamaguchi et al. patent requires two specially interconnected tape portions. Moreover, the turned up end of the reinforcing tape portion causes the folded configuration of the sealing tape to be somewhat bulky.

The adhesive fastener disclosed in U.S. Pat. No. 3,833,456 to Reed et al. can also be attached to both the front and back surfaces of a diaper to provide for force distribution over both surfaces. This particular fastener comprises two co-extensive webs with each web having an adhesive coating extending along substantially all of one face. The lower or base web also has a release coating on one end portion of its opposite face so that a portion of the adhesive coating on the upper web is releasably secured thereto while the rest of the adhesive coating on the upper web bonds the two webs together. Since two substantially co-extensive webs are present, the fastener is bulky in the folded configuration, and is relatively expensive to manufacture.

A similar tape fastener is shown in U.S. Pat. No. 3,848,594 to Buell wherein the tape fastener is also attached to both the front and back surfaces of the diaper while having a securing portion attached to an adjacent section of the diaper, but has the disadvantage in that each tape fastener is comprised of two or more separate tape segments which are joined together so as to produce a common area of joinder for both fastener anchoring legs and the fastener securing portion and thereby adding complexities and expense to the manufacturing process, as well as requiring careful positioning during diaper manufacture.

A problem with many of the above-cited patents is the difficulty in gripping the free end of tab preparatory to fastening the diaper about an infant. The tabs are usually substantially coextensive with an underlying release sheet and quite often the mother or nurse, when preparing to apply the diaper about an infant, tears the release sheet from the diaper and damages the diaper facing instead of separating the free working end of the tab from the release sheet.

SUMMARY OF THE INVENTION

According to the present invention, tape tab fasteners are used on each side of a diaper and are provided with distal gripping means to facilitate separation of the tab fastener from an underlying release means preparatory to fastening the diaper about an infant.

Each tab fastener includes a backing web which is folded over to define two anchoring legs which are permanently attached to a marginal portion of the diaper received therebetween. A face web has a continuous layer of pressure-sensitive adhesive on one face thereof and includes a fixed end permanently attached to the outer face of one leg, a grippable adhesive-free region at the opposite end of the face web, and a free working portion therebetween. The continuous layer of adhesive extends over the fixed end and the free working portion. The free working portion is movable from a folded-over storage position, in which the adhesive layer is releasably attached to a release region provided on the outer surface of the other anchoring leg, to a working position in which the adhesive layer is available to secure the diaper about an infant.

The grippable adhesive-free region extends inwardly away from the lateral margin of the diaper and beyond the end of the release region when the tab fastener is in the storage position. A user can thereby grasp the adhesive-free region and readily separate the free working portion from the release region to make the adhesive-coated free working portion available for use in securing the diaper about an infant.

The tape tab fasteners of the present invention are easily grippable yet remain flat against the diaper when in the folded configuration and will not interfere with the diaper manufacturing machinery and the subsequent folding and packaging operations. Additional features of this invention include the utilization of a tape segment which is relatively easy to affix to the diaper, and which provides good bond strength and permanent attachment of the tab fastener to both the diaper facing sheet and backing sheet.

BRIEF DESCRIPTION OF THE DRAWINGS

FIG. 1 is a perspective view, partially broken away to show interior detail, of an open unfolded diaper in accordance with one of the embodiments of the invention;

FIG. 2 is an enlarged fragmentary cross-sectional view of the diaper of FIG. 1 taken along plane 2—2;

FIG. 3 is an enlarged fragmentary cross-sectional view of the diaper of FIG. 1 taken along plane 3—3.

FIG. 4 is a perspective view of the diaper of FIG. 1 in a configuration assumed by the diaper when placed about an infant;

FIG. 5 is a fragmentary cross-sectional view, similar to FIG. 2, and illustrating an alternate embodiment of the invention; and FIG. 6 is a front elevational view of a tape tab stock from which the individual tabs can be made.

DESCRIPTION OF THE PREFERRED EMBODIMENTS

In the following description, two digit numerals are used to refer to the embodiment illustrated in FIGS. 1–4 and 6 and three digit numerals in the one hundred series are used to refer to the embodiment illustrated in FIG. 5. The same last two digits in each numeral designate similar elements in the various embodiments.

Disposable diaper 10, illustrated in FIGS. 1 and 4, is of substantially quadrilateral configuration and presents inside surface 12 for direction toward an infant and outside surface 14 for direction away from the infant. Adhesive tab fastener means such as tab 16 are attached to diaper 10 for securing diaper 10 about an infant. As described in greater detail below, tab 16 is movable from a folded-over storage position illustrated in FIG. 2 to a working position which is illustrated in FIG. 3.

Referring to FIGS. 1–3, diaper 10 comprises moisture-pervious facing sheet 20, defining diaper inside surface 12 and overlying moisture-retaining absorbent pad 22, and backing sheet 24 which is made of a moisture-impervious material and defines diaper outside surface 14. Absorbent pad 22 is somewhat smaller than the backing sheet 24 and is centrally disposed thereon; however, absorbent pad 22 can be made coextensive with backing sheet 24, if desired. Facing sheet 20 is juxtaposed and preferably substantially coextensive with backing sheet 24. Both the facing sheet 20 and pad 22 can be anchored to the backing sheet 24 by means of adhesive beads 26, glue spots or in any other convenient manner. For example, if backing sheet 24 is made of a thermoplastic material, facing sheet 20 and pad 22 can be attached thereto by heat bonding.

As illustrated in FIGS. 2 and 3, adhesive tab fastener 16 comprises a backing web 28 which is folded over about the marginal edge of diaper 10 so as to define first and second anchoring legs 30, 32 each having an inner face 34 and an outer face 36. Anchoring legs 30, 32 preferably are about equal in width and length, and are in a substantially juxtaposed relationship to one another. Anchoring legs 30, 32 receive a marginal portion of the diaper therebetween, and are provided with an adhesive coating which may comprise a continuous adhesive coating 38 on the inner face 34 thereof. First anchoring leg 30 is permanently attached to facing sheet 20 and second anchoring leg 32 is permanently attached to backing sheet 24 by means of adhesive coating 38 which is substantially coextensive with both anchoring legs 30 and 32. Adhesive coating 38 can be a pressure-sensitive adhesive composition, a heat-activated or solvent-activated adhesive composition, or the like.

Tab fastener 16 further includes face web 40 having fixed end 42, free working portion 44, and a grippable adhesive-free region 45 at the opposite end of the face web. Fixed end 42 of face web 40 is permanently attached to second anchoring leg 32 by means of pressure-sensitive adhesive coating 46 which is provided on the inside face 48 of fixed end 42. Pressure-sensitive adhesive coating 50 is a continuation of coating 46 and is provided on inside face 48 of free working portion 44, faces in the same direction as diaper inside surface 12 when tab fastener 16 is in the working position, and provides a securement means which can be moved from the closed, storage position of FIG. 2 to the open, working position of FIG. 3 for fastening the diaper about an infant.

Release means 52 is provided on anchoring leg 30 and is adpated to be releasably attached to adhesive coating 50. The release means may be a release coating on outer face 36 of first anchoring leg 30 providing a release region facing substantially in the same direction as diaper inside surface 12. When tab fastener 16 is in the storage position of FIG. 2, adhesive coating 50 on free working portion 44 of face web 40 is releasably adhered to release means 52 which is substantially coextensive with adhesive coating 50.

A gripping means facilitates the grasping of tab 16 to separate adhesive coating 50 on free working portion 44 of face web 40 from release means 52 preparatory to fastening the diaper about an infant. As shown in FIG. 2, the gripping means includes a distal adhesive-free region 45 which extends inwardly away from lateral margin 54 of diaper 10 and beyond outermost margin or end 56 of adhesive coating 50. To be easily grippable, adhesive-free region 45 preferably is at least about ⅛ inch in length, more preferably is at least about ¼ of the length of free working portion 44, and also projects inwardly beyond edge 56 of release means 52 when tab fastener 16 is in the folded-over storage position. The adhesive-free region 45 thereby provides a convenient gripping means for separating adhesive coating 50 on free working portion 44 from release means 52 so that free working portion 44 can be moved to the extended working position shown in FIG. 3 in which adhesive coating 50 is available for use in securing the diaper about an infant.

In the embodiment illustrated in FIG. 5, tab fastener 116 includes backing web 128 having anchoring legs 130, 132 provided with release means 152 on outer face 136 of anchoring leg 130, and face web 140 which is divided into fixed end 142, free working portion 144, and adhesive-free region 145 at the opposite end of the face web. Fixed end 142 is permanently attached to the backing web, and a pressure-sensitive adhesive coating or layer 150 is provided on inside face 148 of free working portion 144. A portion 160 of adhesive coating 148 extends beyond edge 156 of release means 152 and beyond innermost edge 162 of anchoring leg 130 when tab fastener 116 is in the storage position. In this position, adhesive portion 160 adheres to diaper facing sheet 120 to retain face web 140 in the folded-over storage position. Adhesive portion 160 is severable from facing sheet 120 for moving free working portion 144 to an extended working position in which adhesive coating 150 is available for securing the diaper about an infant.

As illustrated in FIG. 6, the tabs of the present invention can be manufactured in the form of tape tab stock 65 by laminating, extruding or otherwise fabricating backing web 28, applying an adhesive coating 38 on inner face 34 thereof, and applying release means 52 along a portion 30 of outer face 36 of the backing web. Face web 40 is likewise laminated, extruded or otherwise fabricated and has fixed end 42 permanently attached to portion 32 of backing web 34 by means of pressure-sensitive adhesive coating 46 which is provided on the inside face 48 of fixed end 42. Face web 40 also includes an adhesive-free region 45 at the opposite end thereof, and a free working portion 44 situated between fixed end 42 and adhesive-free region 45. Pressure-sensitive adhesive coating or layer 50 is continuous with coating 46, is provided on inside face 48 of free working portion 44, and is releasably attached to release means 52 which is substantially coextensive therewith. Adhesive-free region 45 is grippable and extends beyond edges 56 and 57 of adhesive coating 50 and release means 52, respectively.

If outer face 66 of face web 40 does not have inherent release properties, a backing sheet 68 (FIG. 6) can be releasably attached to adhesive coating 38 on backing web 28, so that tape stock 65 can be rolled longitudinally into a form suitable for storage and shipping. Tape stock 65 can then be transversely severed along its length to produce individual tab fasteners 16.

To facilitate the application of tab fasteners 16 to the diapers on high speed production machinery, backing sheet 68 includes a protruding end portion 70 which extends beyond edge 62 of backing web 30. Since there is a space A between end portion 70 of backing sheet 68 and adhesive-free region 45 of face web 40, which space corresponds to the total thickness of backing web 28, release means 52, and adhesive coatings 38 and 50, backing sheet 68 can be more readily grasped and removed from tab 16 by the tab applicator machinery during the production of the diapers.

Release means such as region 52 in FIG. 3 may comprise a ribbon segment or release strip carried by backing web 28 and provided with a release coated face 76 which provides the release region, and an adhesive coating on opposite face 78 by means of which the release strip is anchored to first anchoring leg 30 of backing web 28. Release coated face 76 faces in the same direction as diaper inside surface 12 and is substantially coextensive with adhesive coating 50 on free working portion 44 of face web 40 when tab 16 is folded to the storage position. Alternatively, release means 52 may comprise a release coating, such as a silicone release compound, or the like, on the outer face 36 of first anchoring leg 30 of backing web 28 and which is substantially coextensive with adhesive coating 50 on free working portion 44 of face web 40 when tab fastener 16 is folded to the storage position.

Adhesive tab fasteners suitable for the purposes of the present invention can be made from a wide variety of materials, provided that such materials are sufficiently flexible. Preferred materials for this purpose are polyalkylene webs such as polyethylene sheet, polypropylene sheet, and the like. Particularly preferred are webs which are oriented along the narrow dimension of the tab or webs which have filament reinforcements therein.

The pressure-sensitive adhesive layers such as adhesive coating 50 are provided by applying a coating of a pressure-sensitive adhesive composition known in the art to the appropriate surface of tab 16. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like.

Anchored release strips can be made from smooth plastic film having a relatively non-adhering surface, from paper coated with a silicone release compound, or from similar release materials. A number of appropriate release coatings may be used with the present invention. Examples of such coatings are disclosed in U.S. Pat. No. 2,822,290 to Webber; U.S. Pat. No. 2,880,862 to Sermattei; and U.S. Pat. No. 2,985,554 to Dickard.

Several different types of facing materials may be used for diaper facing sheet 20. For example, facing sheet 20 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 20 may also be made of an apertured, nonwoven fabric which is formed, for example, in accordance with the teachings of commonly assigned U.S. Pat. Nos. 2,862,251, 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd$^2$.

In addition, facing sheet 20 can be formed of a nonapertured material, such as a nonwoven isotropic web, or the like. In all of the aforementioned facing materials, the material should be relatively hydrophobic so as to retard wicking within the facing layer. Also suitable are porous polymeric sheet materials such as polyalkylene webs having a fibrous surface, and the like.

Highly moisture-absorbent fibrous pad or batt 22, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet 24 and facing sheet 20.

A suitable backing sheet material for the diapers embodying the present invention can be opaque polyethylene web about 0.001" thick. Another suitable material for this purpose is a polyethylene terephthalate web having a thickness of about 0.0005". Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

In use, a diaper equipped with the adhesive fasteners of the present invention is applied to the infant by laying out the diaper on a suitable flat surface and placing the infant thereon so that the waist-underlying end of the diaper is that having the tab fastener means. The other end of the diaper then extends downwardly between the infant's legs. Next, the downwardly extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling free end 44 of face web 40 away from its temporary engagement with release means 52, exposing adhesive coating 50 which was releasably adhered to release means 52 and separable therefrom. The tabs are then used to secure the diaper in the desired position by simply urging the pressure-sensitive adhesive surfaces in contact with the adjacent outer surface of the diaper. The applied diaper assumes the configuration illustrated in FIG. 4.

The foregoing description and the drawing are illustrative but are not to be taken as limiting. Still other variations and modifications are possible without departing from the spirit and scope of the present invention.

What is claimed is:

1. A disposable diaper having a facing sheet defining a diaper inside surface for direction toward an infant, a moisture-impervious backing sheet juxtaposed with said facing sheet and defining a diaper outside surface, an absorbent panel positioned between said facing sheet and said backing sheet, and a pair of adhesive tab fasteners each comprising:

a backing web folded over to form first and second anchoring legs each having an inner face and an outer face, said backing web extending around and receiving a portion of the lateral margin of the diaper therebetween, and said inner face of said anchoring legs being provided with an adhesive coating by means of which said anchoring legs are permanently attached to the diaper marginal portion;

a face web having a fixed end, a grippable adhesive-free region at the opposite end of said face web, and a free working portion situated between said fixed end and said adhesive-free region, a continuous layer of pressure-sensitive adhesive being provided on one face of said face web and coextensive with said fixed end and said free working portion, said fixed end being permanently attached to said second leg by means of said adhesive layer; and release means releasably attached to said adhesive layer on said free working portion;

said grippable adhesive-free region extending inwardly away from said lateral margin of the diaper and beyond said release means and said backing web when the tab fastener is in a storage position, and said free working portion being separable from said release means to make said free working portion available for use in securing said diaper about an infant.

2. The disposable diaper as defined in claim 1 wherein said release means is carried on said outer face of said first anchoring leg and provides a release region facing in the same direction as said diaper inside surface;

said free working portion being movable from the folded-over storage position wherein said free working portion is releasably adhered to said release region to a working position wherein said free working portion of said tape segment is available for use in securing said diaper about an infant.

3. The disposable diaper as defined in claim 2 wherein said release region is substantially coextensive with the portion of said adhesive layer on said free working portion.

4. The disposable diaper as defined in claim 2 wherein a portion of the pressure-sensitive adhesive layer extends beyond said release region and adheres to said facing sheet to retain said face web in said folded-over storage position but is severable from said facing sheet for moving said free working portion to said working position.

5. The disposable diaper as defined in claim 2 wherein the portion of said layer of adhesive on said free working portion faces in the same direction as said diaper inside surface when said tab fastener means is extended to said working position.

6. The disposable diaper as defined in claim 2 wherein said release means is a release coating on said outer face of said first anchoring leg.

7. The disposable diaper as defined in claim 6 wherein said release coating comprises a silicone release compound.

8. The disposable diaper as defined in claim 2 wherein said release means comprises a ribbon segment which has one face adhesively affixed to the outer face of said first anchoring leg and an opposite face having a release coating.

9. The disposable diaper as defined in claim 1 wherein said face web is adhesively attached to said backing web.

10. The disposable diaper as defined in claim 2 wherein said grippable adhesive-free region extends for a distance which is at least about ⅛ of the length of said free working region.

* * * * *